Figure 1:
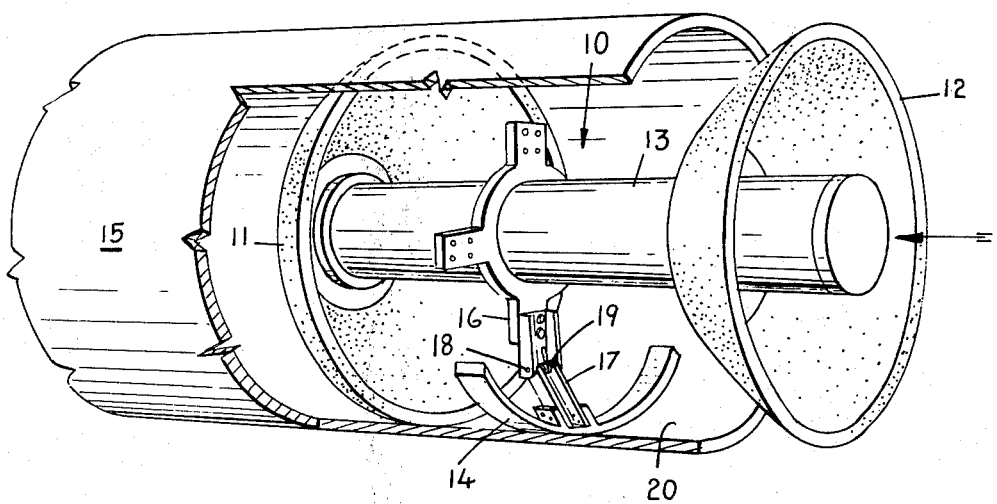

United States Patent [19]

Porter

[11] 3,973,441
[45] Aug. 10, 1976

[54] ACCELEROMETER PIG
[75] Inventor: Patrick C. Porter, Rexdale, Canada
[73] Assignee: Trans Canada Pipelines Limited, Toronto, Canada
[22] Filed: Nov. 14, 1975
[21] Appl. No.: 631,934

[30] Foreign Application Priority Data
Nov. 12, 1975 Canada .................................. 239395

[52] U.S. Cl. ................................. 73/432 R; 73/105
[51] Int. Cl.$^2$ ........................................... G01B 5/28
[58] Field of Search .................. 73/432 R, 151, 488, 73/49.5, 105

[56] References Cited
UNITED STATES PATENTS
2,884,624  4/1959  Dean et al. ................... 73/432 R UX
3,495,546  2/1970  Brown et al. .................... 73/432 R X
3,786,684  1/1974  Wiers ................................. 73/432 R

*Primary Examiner*—Jerry W. Myracle

[57] ABSTRACT

A pipeline pig adapted to carry inspection components to determine flaws in a pipeline wall arising from corrosion, pitting, gouges, hard spots, scratches, metallurgical anomalies and dents causing out of round conditions is equipped with an accelerometer. The accelerometer is adapted to provide an electrical signal indicative of acceleration and deceleration in the direction parallel to the axis of the pipeline. By correlation of signals recorded by the flaw detection equipment with signals recorded from the accelerometer, dents may be readily identified.

6 Claims, 3 Drawing Figures

U.S. Patent   Aug. 10, 1976   3,973,441

ACCELEROMETER PIG

This invention relates to improvements in pipeline pigs commonly used for a variety of purposes in fluid-carrying pipelines.

The pipeline industry conventionally utilizes pipeline pigs to accomplish certain specialized operations inside pipelines. Commonly, pipeline pigs include an elongated body which is retained centrally of the pipeline by two or more flexible, radially outwardly extending scraper cups spaced apart longitudinally and fitting snugly but slidably (due to their resilience) within the pipeline.

Pipeline pigs are forced through the pipeline by pressure from the fluid behind the pig exerted on the body of the pig and on the scraper cups attached thereto.

The body of a pipeline pig can support brushes, scrapers, or other devices for cleaning the interior wall of the pipeline. Other pipeline pigs do not carry cleaning elements, but are used simply as separation pigs for separating two different fluids being consecutively passed through the pipeline. Still other pipeline pigs are used to remove fluid trapped at low spots in the pipeline. There are also in use certain kinds of pipeline pigs which carry checking and measuring instrumentation through the pipeline to measure fluid characteristics, to check the pipeline itself, or to accomplish any of a large number of measurements or safety checks necessary to the proper maintenance and operation of a pipeline.

It is to this latter group of pipeline pigs, those carrying instrumentation through the pipeline, that this invention particularly relates.

SUMMARY OF THE INVENTION

The invention comprises the combination of a pipeline pig adapted to be moved through a pipeline, the pig having sensing means associated therewith for measuring various characteristics of the pipeline which sensing means have an electrical output which is indicative of the condition being sensed, an accelerometer and a recording device on which signals from the accelerometer indicative of axial acceleration of the pig within the pipeline and signals from the sensing means are recorded.

Most pigs which are adapted to inspect the condition of the pipeline are equipped with a series of sensors. These sensors may be adapted to provide a magnetic inspection or sonic inspection of the pipe wall. Usually, a series of sensors are used in order that the entire circumference of the pipeline may be inspected as the pig passes along the pipeline. The output signal from the sensors is often fed into some form of multichannel recording device which is carried within the pig. By inspection of the recorder after a run by the pig, flaws may be located if the location of the pig can be determined at the time when the flaw was sensed. The type of flaws sensed by the pig particularly if a magnetic inspection is used will include cracks in the wall of the pipeline, metallurgical anomalies such as hard spots, gouges and scratches on the exterior of the pipeline as may be caused during placing the pipeline in its trench, and corrosion flaws. The sensors will also detect areas of changing magnetic flux as a result of alteration of metallurgical properties in the pipe wall. As the sensors pass over welds in the pipe a signal arising from the particular sensor that passes over the welds will be recorded. In the event of weld icicles within the pipe the sensors will also indicate a change in magnetic properties.

One of the more dangerous flaws which may result in failure of a pipeline is the physical crushing of the pipe possibly as a result of the back filling operation when the pipe is installed in its trench. In the event the pipe is subjected to a severe load a dent will be caused on the pipe which will mean that the pipe is no longer round. These out of round conditions may consist of buckles, dents, ovalling or similar defects. Such out of round condition may mean that the steel forming the pipeline has been worked while in the cold state and accordingly, may not be dependable at the pressures at which the pipeline is to be operated. As indicated above, the sensors of pigs conducting a magnetic inspection of the pipe wall may sense an out of round condition and provide an output signal to be recorded by the recording means. However, it is extremely difficult to interpret the output signal of the sensor in order to distinguish between the various types of flaws. Accordingly, it would be of significant advantage in interpreting the output of the various sensors of a pipeline inspection pig if the out of round flaws could be readily identified on the recording device.

According to this invention an easy method is provided whereby out of round flaws may be distinguished from other flaws detected by a magnetic inspection device. In order to identify an out of round condition in a pipeline, the pipeline pig is equipped with an accelerometer. An accelerometer is the device which provides an electric output signal which is proportional to the acceleration being applied to the device. For use with a pipeline pig the accelerometer is installed in the pig such that its signal will only record accelerations and decelerations in the axial direction. It will be obvious to those skilled in the art that a pipeline pig will travel up and down as the pipeline travels over hills and through valleys. Accordingly, there will be many accelerations and decelerations applied to the pig but only those in the direction along the axis of the pipeline are considered relevant to the out of round condition.

As a pipeline pig being propelled through a pipeline by pressure of the pipeline fluid acting against scraper cups, encounters an out of round spot in the pipeline the axial velocity of the pig in the pipeline will be reduced resulting in a deceleration. Accordingly, if a pig is equipped with an accelerometer the accelerometer will sense the change in velocity of the pig and this change in velocity may be recorded on the multi-channel recording device along with the signals from the various sensing devices. Thus, when examining the record of a pig run, out of round conditions may be readily identified by comparing the flaw signal produced by the sensing devices with the output signal produced by the accelerometer.

Figure 2:
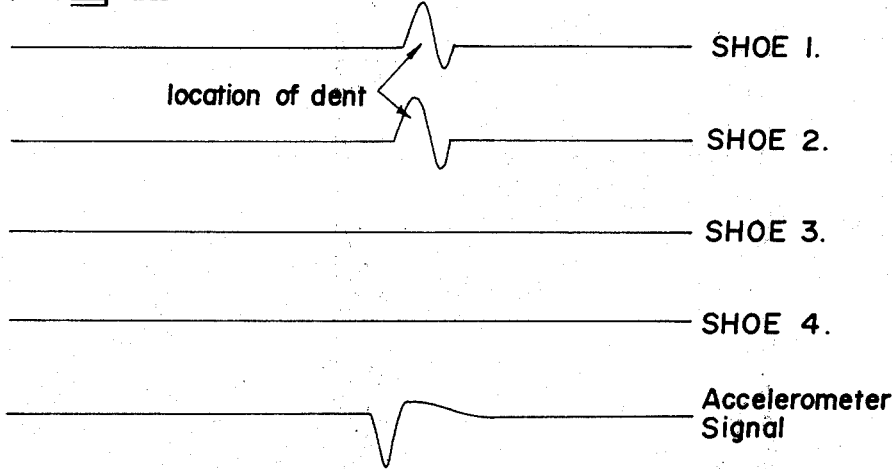
Figure 3:
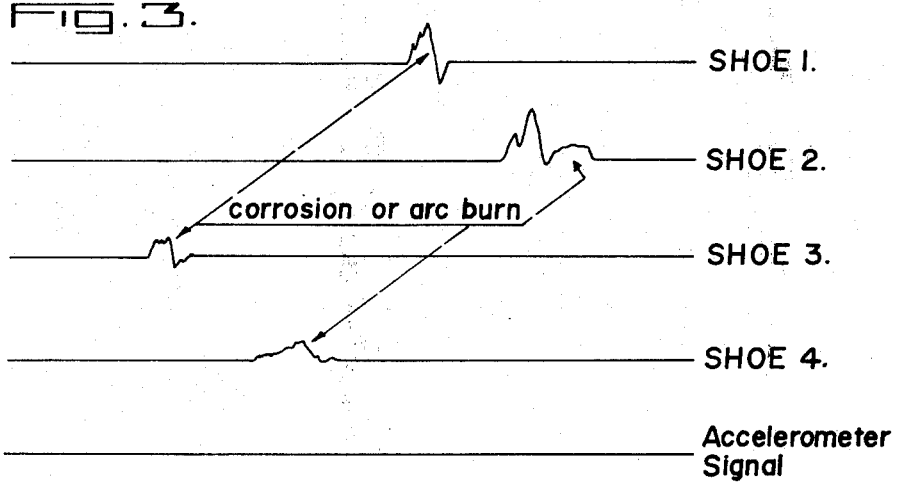

The invention will now be explained by reference to the attached drawings, in which;

FIG. 1. is a view of an instrument carrying inspection pig;

FIG. 2. is an illustration of the type of signal that may be recorded when an out of round condition is encountered; and FIG. 3. is an illustration of the type of signal that may be recorded when there is no out of round condition.

FIG. 1 illustrates an example of an instrument carrying inspection pig. The pig 10 comprises a scraper cup 11 located at one end thereof and a second scraper cup 12 located at the opposite end thereof. The two scraper cups 11 and 12 are mounted on a body portion 13. Scraper cups 11 and 12 support the body portion 13 and convey it through the pipeline. The scraper cups also serve to propel the pig 10 through the pipeline 15. It will be obvious to those skilled in the art that the location of the scraper cups with regard to the pig body and the number of scraper cups which may be used may vary according to the size or weight of the pig body 13. In the embodiment shown in FIG. 1 an annular array of inspection shoes is arranged about the body of the pig. Inspection shoes 14 are attached to the pig body 13 by means of bracket 16 and movable arms 17. Movable arms 17 are pivotted at 18 and spring means 19 will urge the shoes 14 into contact with the inner circumference 20 of the pipeline wall. For the purposes of clarity only one such shoe 14 is illustrated. However, it will be obvious from the figure that a series of shoes will be used in order to inspect the entire circumference of the pipeline. Each of shoes 14 will include inspection devices which may include magnetic inspection devices comprising magnets and coils or sonic inspection devices. Other means of inspection of the inner circumference of the pipeline will be well known to those skilled in this art.

In the body 13 of the pipeline pig 10 there is located a compartment containing suitable electronic or other apparatus to perform the inspection function. Also located within the pig body 13 is an accelerometer and a multi-channel recording device.

The accelerometer used is not shown. Accelerometers suitable for this purpose are commercially available and generally consist of a balanced resistive, strain gage bridge. An example of a suitable available accelerometer is the Statham Model No. AG69TC-10-350. Depending on the input level required by the recording device, the output of the accelerometer will likely be amplified.

In most instances a series of shoes will be used to inspect the entire circumference of the pipeline wall. However, in some instances, it may be that a singular annular sensor is used. In any event, a recorder must be used to record the output from the sensor or sensors as the case may be. Typically, a signal is also generated and recorded by the recorder which indicates the distance or time the pig has been in operation. Thus, by correlation with the distance signal, flaws sensed by the sensing device may be located within the pipeline. Thus, the recorder normally must have at least two channels and preferably may have several more. The recorder required for the purposes of this invention must have a separate channel to permit recording of the output signal from the accelerometer.

FIG. 2 illustrates the type of signal which may be recorded by a multi-channel recorder when used in conjunction with pig comprising four inspection shoes. In this illustration the output signal from each of the four shoes is separately recorded by the recording device as is also the output signal from the accelerometer. The channel recording the distance signal is not shown. When the pig encounters an out of round condition various signals will be produced as shown in FIG. 2. Because of the out of round condition the shoe or shoes moving over the dent will not be in close contact with the pipe wall over the full length of the shoe and this will typically produce an output signal from that shoe. In FIG. 2 it is assumed that the dent is large enough to produce an output from each of shoe 1 and shoe 2. However, the dent is not so large as to produce an output from either shoe 3 or shoe 4. As explained above, on encountering the out of round condition the pig will decelerate providing a negative signal from the accelerometer. If the deformation is extreme, than the pig may come to a complete stop. In any case, the pressure behind the pig will increase slightly and push the pig past the obstruction whereupon it accelerates until it reaches the previous speed. Thus, in FIG. 2 the channel recording the output of the accelerometer indicates a sharp negative acceleration or deceleration followed by a small positive acceleration. The deceleration encountered is a function of the speed of the pig and the size of the deformation. The faster the pig is going prior to encountering the out of round condition, the more it is able to decelerate, and the greater will be the negative going spike or shock. In this way, it is possible to judge the size of the dent by examining the signal from the accelerometer.

FIG. 3 illustrates the detection of typical flaws by the inspection shoes which are not associated with deformation of the pipe. These flaws could be due to corrosion, arc burns, or a lamination in the wall. In this case, the flaw signals are recorded by the various channels recording the output from the sensor shoes, but there is no output from the accelerometer since the pig continues at a uniform velocity.

The signals illustrating the flaws sensed in FIGS. 2 and 3 are not necessarily typical as far as their shape is concerned. The signals are merely illustrated as it is their presence or absence which is the most important factor.

Accordingly, by use of an accelerometer in a pipeline pig equipped with sensing devices, an out of round condition may be determined from a record produced by a multi-channel recorder. It will obvious to those skilled in the art that the number of channels selected, the type of sensing device or the type of accelerometer used may all be varied without departing from the scope of the invention as defined in the attached claims.

What I claim is:

1. In combination a pipeline pig, said pig being adapted to be moved along a pipeline and to carry at least one device for inspecting the condition of the wall of a pipeline from within the pipeline, said inspection device providing an electrical signal indicative of changes in the condition being sensed, an accelerometer adapted to provide an electrical signal indicative of acceleration and deceleration of said pig in the direction parallel to the axis of said pipeline, and a recorder, said recorder being adapted to record the signal from said inspection device and the signal from said accelerometer.

2. The combination of claim 1, wherein the inspection device is adapted to sense changes in the magnetic characteristics of the wall of said pipeline as said pig moves through said pipeline.

3. The combination of claim 2, wherein said recorder is adapted to record the signal from said inspection device discretely from the signal from said accelerometer.

4. A pipeline pig comprising:
a body portion,
scraper cups mounted on said body portion, said cups adapted to contact the inner wall of a pipeline such that fluid passing through said pipeline will convey said pig along said pipeline, a plurality of magnetic inspection devices attached to said body portion and adapted to detect changes in magnetic flux within said pipeline as said pig passes along said pipeline and provide an electrical signal indicative of said changes, magnetic means attached to said body portion adapted to induce a magnetic field in said pipeline, an accelerometer mounted within said body portion and adapted to provide an electrical signal indicative of acceleration and deceleration in a direction parallel to the direction of travel of said pig, and recording means mounted within said body portion adapted to record the signals from said plurality of inspection devices and said accelerometer.

5. A method of detecting out of round conditions in a ferrous pipeline comprising passing a pipeline pig through said pipeline to be inspected, said pipeline pig being adapted to carry at least one inspection device which device provides an electrical signal indicative of changes in the metallurgical condition of the wall of said pipeline, said pig also being adapted to carry an accelerometer, which accelerometer provides an electrical signal indicative of acceleration and deceleration of said pig in the direction parallel to the axis of said pipeline, and recording the signal of said inspection device and said accelerometer on separate channels of a common recording device carried by said pig.

6. The method of claim 5 wherein said pig is moved through said pipeline by the pressure of fluid flowing within said pipeline acting against resilient deformable scraper cups which are attached to said pig and contact the interior circumference of said pipeline.

* * * * *